US00PP30669P3

(12) United States Plant Patent
Hansen

(10) Patent No.: US PP30,669 P3
(45) Date of Patent: Jul. 9, 2019

(54) ***BAPTISIA* PLANT NAMED 'PINK LEMONADE'**

(50) Latin Name: ***Baptisia* hybrid**
Varietal Denomination: Pink Lemonade

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 31 days.

(21) Appl. No.: 15/732,458

(22) Filed: Nov. 15, 2017

(65) Prior Publication Data

US 2019/0150347 P1 May 16, 2019

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
CPC ..... A01H 5/02
See application file for complete search history.

(56) References Cited

PUBLICATIONS https://www.finegardening.com/article/episode-2-whats-on-my-plant-list-this-year; Apr. 26, 2017; 9 pages.*

* cited by examiner

*Primary Examiner* — Kent L Bell

(57) ABSTRACT

A new and distinct plant of hardy herbaceous false indigo named *Baptisia* 'Pink Lemonade' characterized by having light yellow flower buds developing strong blushing of clear raspberry-purple on open flowers on long spikes. The new plant has tall, multi-stemmed, vase-shaped, winter-hardy habit with glaucous medium-green tri-foliate foliage and is suitable for landscaping as a specimen or en masse.

1 Drawing Sheet

Botanical classification: *Baptisia* hybrid.
Cultivar designation: 'Pink Lemonade'.

BACKGROUND OF THE INVENTION

The present invention relates to a new and distinct cultivar of hybrid *Baptisia* plant, botanically known as *Baptisia* 'Pink Lemonade' and will be referred to hereafter by its cultivar name, 'Pink Lemonade'. The new cultivar represents a new false indigo, a hardy herbaceous perennial grown for landscape and cut flower use.

The new invention arose from an ongoing breeding program of the inventor at a nursery in Waseca, Minn. with continued evaluation at a wholesale perennial nursery in Zeeland, Mich. with the specific intention of improving garden worthiness of perennial false indigo plants with a wider variety of flower colors and improved garden habit.

*Baptisia* 'Pink Lemonade' was a single seedling selection from many seedling among an open pollination between *Baptisia* 'Red Riding Hood' (not patented) as the female and an unknown male or pollen parent presumed to be *Baptisia alba* or a hybrid containing *Baptisia alba* from an isolation block.

Seeds were collected from the individual selected female plant on Oct. 29, 2009 at the isolation breeding block in Waseca, Minn., USA by the inventor. The seeds were sown at a wholesale perennial nursery in Zealand, Mich., USA with initial and final evaluations being completed at the same nursery in Michigan. Ultimately, prior to naming the new plant was given the breeder code H9-51-06.

No plants of *Baptisia* 'Pink Lemonade' have been sold, under this or any name, in this country or anywhere in the world, prior to the filing of this application, nor has any disclosure of the new plant been made prior to the filing of this application with the exception of that which may have been disclosed or sold within one year of the filing of this application and was either derived directly or indirectly from the inventor.

'Pink Lemonade' was initially asexually propagated by stem cuttings at a nursery in Zeeland, Mich., USA in 2013. The resultant plants have demonstrated that the new plant has remained stable and true to type in successive generations of asexual propagation.

The nearest comparison plant known to the inventor is 'Solar Flare' U.S. Plant Pat. No. 20,408. Compared to 'Solar Flare' the new plant is taller and more vase-shaped in habit, and the flowers of the new plant are lighter yellow in bud becoming clear raspberry purple as opening while 'Solar Flare' produces buds of a deeper yellow that become more orange-purple or brown. In comparison to 'Pink Truffles' U.S. Plant Pat. No. 26,588, the flower color of the new plant begins light yellow and develops clear raspberry-purple, whereas the flower buds of 'Pink Truffles' start darker pinkish-violet and open to a lighter pinkish lavender. Compared with the female parent, the new plant has two-tone colored flowers. Other similar cultivars include 'Cherries Jubilee' U.S. Plant Pat. No. 23,907 and 'Lemon Meringue' U.S. Plant Pat. No. 24,280. Compared with 'Cherries Jubilee' the new plant has lighter yellow buds and less brownish-red flowers. Compared with 'Lemon Meringue' the new plant has lighter yellow buds and develops flowers with clear raspberry-purple flowers. The new plant is also taller than both 'Lemon Meringue' and 'Cherries Jubilee'.

The new plant differs from all *Baptisia* known to the inventor in the following combined traits:

1. Young flower buds of light yellow developing blushing of raspberry-purple.
2. Flowers open to a clear raspberry-purple.
3. Tall, vase-shaped, multi-stemmed, winter-hardy habit.
4. Glaucous, medium-green, tri-foliate foliage.

BRIEF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of a seven-year-old plant growing in an open full-sun trial garden in Zeeland, Mich.

DETAILED BOTANICAL DESCRIPTION OF THE PLANT

Figure 1:
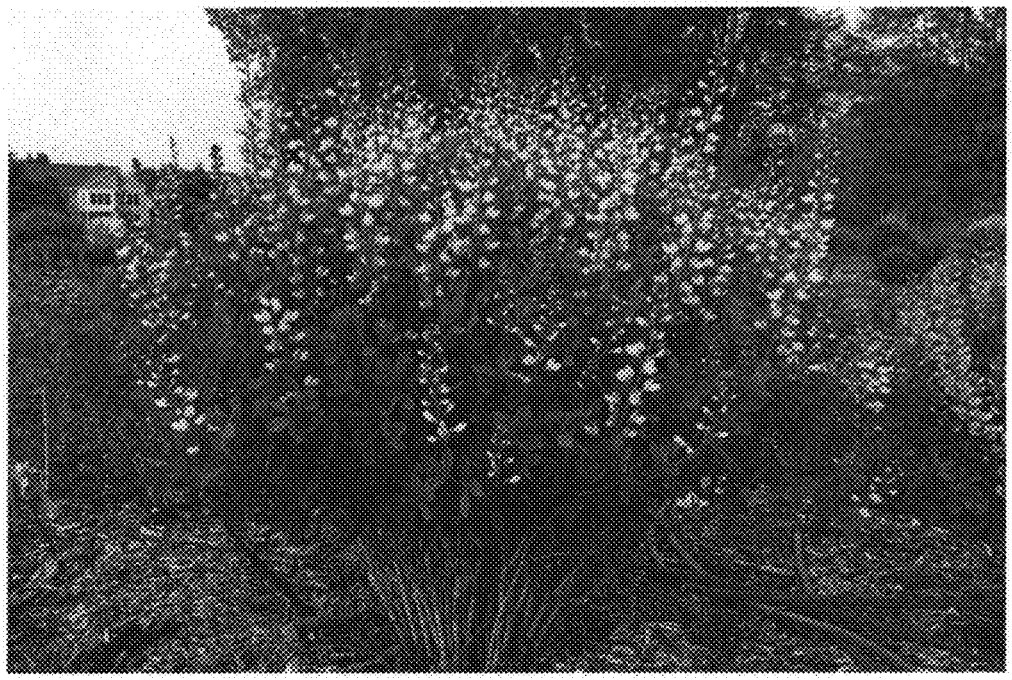
FIG. 1 shows the habit of a plant in full flower.
Figure 2:
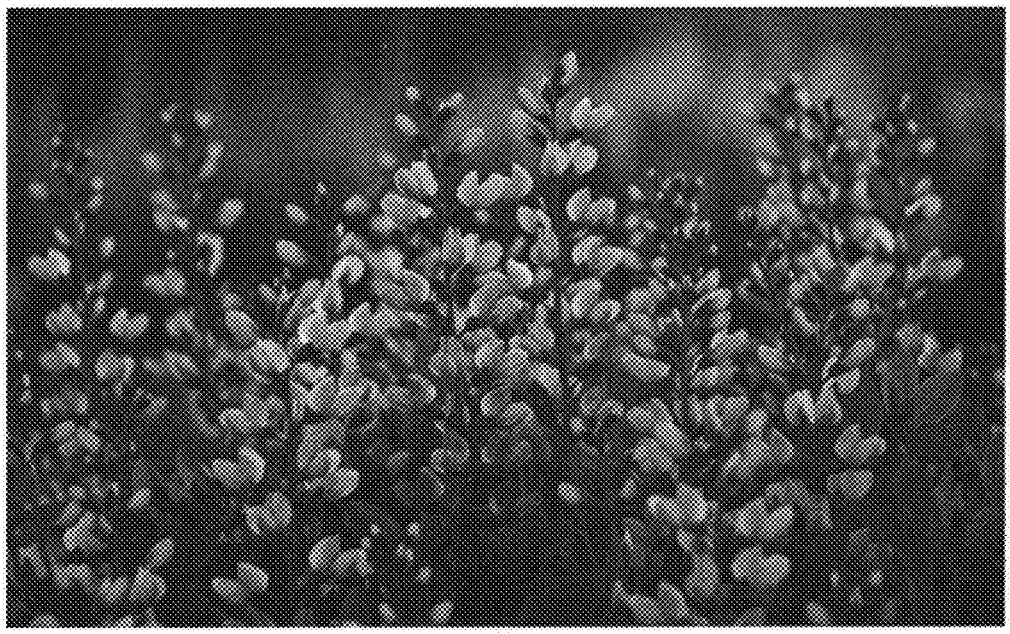
FIG. 2 shows a close-up of the flower scape with open flowers and buds.

The following is a detailed description of a seven-year-old plant of the new cultivar as grown outdoors in a trial plot at a wholesale nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, well-branched, many-stemmed, vase-shaped growth habit with long inflorescences held above the foliage;

Plant size: Stems and crown about 32 cm across at soil level, about 146 cm tall from soil to top of flowers and 140 cm wide just below initial flowers;

Roots: Fibrous, well-branched, long, deeply rooted;

Root color: Nearest RHS 161D;

Propagation method: Stem cuttings, rooting in about three weeks;

Growth rate: Moderate, similar to other *Baptisia;*

Stems: Rigid and mostly upright; highly glaucous; glabrous; terete; lower two to three nodes without leaves or branches; normally 75 to 90 stems per plant; main stem to about 12.0 mm diameter at base and 146 cm tall to top of inflorescence, average about 140 cm long and about 9.5 mm diameter;

Branches: Normally about five alternately-arranged primary branches at 45 to 60 degree angle above horizontal, up to 62.0 cm long and 6.5 mm diameter, average for primary branches about 38.0 cm long and 6.0 mm diameter, smaller distally; and three alternately-arranged secondary branches per stem of about 24 cm long and 4.0 mm diameter, averaging about 20.0 cm long and 3.5 mm diameter;

Stem color: Between RHS 191B and 138B;

Stem scales: At stem nodes; slightly glaucous; dehiscing to leave behind thin scar; about 4.6 cm long and 18.0 mm wide at base and about 20.0 mm wide in center; frequently with apical three leaflets about 6.0 mm long and 2.0 mm wide in center of retuse apex with sharply pointed sides; truncate base;

Stem scale color: Blend between RHS 79B and RHS N189B before dehiscing and nearest RHS N200A after dehiscing;

Internodes: Up to 9.5 cm apart between lowest branches, average about 6.8 cm;

Foliage: Alternate on stem; ternate to palmately compound with three leaflets; outer two leaflets at about 60 to 80 degree angle to middle leaflet, increasing with leaf age; up to 5.4 cm long and 9.3 cm wide, average 4.6 cm long and 6.2 cm wide;

Leaflet: Three, oblanceolate; apex acute, base attenuate; margins entire; petiolate; adaxial surface matte, scaberulose abaxial; size up to about 5.2 cm long and about 2.2 cm wide, average about 4.0 cm long and 2.0 cm wide;

Leaflet color: Newly expanding nearest RHS 146B abaxial and adaxial surfaces; mature upper surface nearest RHS 137C and abaxial nearest RHS 138A;

Venation: Pinnate; glabrous; thin, not conspicuous;

Vein color: Same color as surrounding leaf tissue abaxial and adaxial; basal half of abaxial midrib nearest RHS 148C;

Petioles: Glabrous; slightly glaucous; concaved adaxial, rounded abaxial; up to about 7.0 mm long and 2.0 mm wide, average 5.0 mm long and 1.8 mm wide;

Petiole color: Nearest 146C abaxial and nearest RHS 146B adaxial;

Stipules: Narrowly lanceolate, acute apex with base truncate to stem; up to 2.6 cm long and 12 mm wide, average 2.0 cm long and 10.0 mm wide with largest stipules below primary branches and decreasing distally and on secondary branches;

Stipule color: Nearest RHS 138A both surfaces;

Flower: Zygomorphic, papilionaceous, non-secund, held at about 45 degree angle above horizontal; about 75 flowers per main raceme and about 35 per secondary branch; seasonally effective for about 3 to 4 weeks beginning in late May to early June in Zeeland, Mich.; individual flower remain effective and on raceme for about four days; individually about 2.2 cm long, 1.5 cm tall and 1.2 cm wide at tallest and widest portions; an upper banner, a lower keel made up of two lobes folded around gynoecium and androecium; and two lateral wings or alae laterally appressed against keel;

Flower fragrance: None detected;

Peduncle: Rounded with vertical ridges and furrows; glaucous; glabrous; from first flower to apex about 64.0 cm long; diameter at the base of first flower about 5.0 mm and about 2 mm diameter at the apex;

Peduncle color: Nearest RHS N138A at base and nearest RHS N138A with tinting of between RHS N187B and RHS N187A in upper portions, where exposed to higher light levels;

Pedicel: Terete, glabrous, glaucous; about 9.0 mm long and 1.0 mm diameter;

Pedicel color: Nearest RHS N138B with tinting of nearest RHS N187B in upper portions or where exposed to more light;

Calyx: Campanulate; adpressed along petals; four-lobed with lobes dissected about 2.5 mm deep and fused in basal about 5.5 mm; top sepal about 5.0 mm across, side sepals about 2.5 mm across and lower sepal about 3.0 mm across at fusion; apex acute, base fused in basal two thirds;

margins entire; glaucous and glabrous both surfaces; about 8.0 mm long and 7.0 mm across at apex; persists after petal drop;

Calyx color: Abaxial nearest RHS 146C with slight blushing of nearest RHS 183C in regions with more light exposure; adaxial nearest RHS 146D;

Buds one day prior to anthesis: Oblong ellipsoid, flatted vertically; about 21.0 mm long and 10.0 mm tall and 8.0 mm wide near base;

Bud color: Three to four days prior to opening exposed banner petal nearest RHS 3C tinted with nearest RHS 147C;

Petals: Five; consisting of a lower fused keel, an upper banner, and two lateral wings or alae; keel comprised of two sections folded around stamens and pistil;

*Banner petal.*—Conduplicate, curved upward and backward, reflexed to the point of touching side margins; apex retuse; base claw-like; margin entire; about 18.0 mm long, about 18.0 mm across at widest, claw portion about 5.0 mm long and narrowing to about 1.0 mm at base.

*Banner color.*—Young adaxial between RHS 2B and RHS 2C with center rib of nearest RHS 145C and speckling mid petal nearest RHS 187A, abaxial longitudinal center about 3.0 mm wide nearest RHS 145C, surrounded by RHS 2C and distally nearest RHS 2D with blush of nearest RHS 86A; before dehiscing adaxial banner nearest RHS 158D strongly blushed and veined with nearest RHS 83C, center and claw blend between RHS 195A and RHS 152D; abaxial banner nearest RHS 158D blushed and veined with nearest RHS 83C, center and claw nearest RHS 146C.

*Alae* (*lateral wings*).—Oblong blade with short claw; apex rounded; margin entire; blade base auriculate; claw base curved upwardly; about 6.0 mm long and about 1.0 mm across at base; blade about 17.0 mm long and about 7.5 mm across in middle; total length about 21.0 mm long.

*Alae color.*—Young adaxial blade nearest RHS 2C, claw nearest RHS 145C; young abaxial blade nearest RHS 3D and claw nearest RHS 145C; before dehiscing adaxial blade nearest RHS 11A strongly blushed with RHS N77C; before dehiscing abaxial blade nearest RHS 2D distally, nearest RHS 1D proximally with heavy blushing nearest RHS N77C.

*Lower keel.*—Two petals, fused about 3.0 mm from apex for about 6.0 mm; apex rounded; blade base auriculate; claw about 5.0 mm long and about 1.0 mm across at base; curved upward; total length about 21.0 mm long with blade about 9.0 mm across near middle.

*Keel color.*—Young adaxial and abaxial blade nearest RHS 1C, adaxial and abaxial claw between RHS 145D and RHS 1454C; before dehiscing adaxial blade nearest RHS 157C with blushing of nearest RHS N77C, abaxial distal blade nearest RHS 11B and proximally nearest RHS 1D with heavy blushing of nearest RHS 187B on upper margin.

Receptacle: Disk-shaped, about 3.5 mm diameter and 1.5 mm depth; color blend of RHS 139A and RHS N198A;

Gynoecium: One, with superior ovary;

*Pistil.*—Stalked; about 20.0 mm long and 1.5 mm wide; color listed separately below.

*Style.*—Terete; tapered, narrowing distally; about 8.0 mm long and less than 1.0 mm diameter; color nearest RHS 145A.

*Stigma.*—Minute; about 0.2 mm diameter; color nearest RHS 155A.

*Ovary.*—Superior; terete; suspended by stipe; about 7.0 mm long and about 1.5 mm in diameter; color nearest RHS 143C.

*Stipe.*—Terete; about 5.0 mm long and 0.7 mm diameter; color nearest RHS 145A.

Androecium:

*Stamens.*—Ten; not united; slightly curved upward; about 21.0 mm long and 1.0 mm diameter.

*Filament.*—About 19.0 mm long and 1.0 mm in diameter; slightly curved upward at tip; color nearest RHS 145C.

*Anther.*—Ellipsoidal; basifixed, longitudinal; about 2.0 mm long and 1.5 mm wide; color nearest RHS 16A.

*Pollen.*—Spherical; abundant; color nearest RHS 17A.

Fruit: Bivalve inflated pod; glabrous; about 27.0 mm long, 12.5 mm across and 12.0 mm thick; rounded apex with rostrum about 6.0 mm long and about 0.8 mm thick at base and rounded base with stipe about 15.0 mm long and 1.0 mm diameter;

Fruit color: At maturity nearest N200A;

Seeds: About 12 per flower (open pollinated); reniform; semi-microscopic papillose; about 4.5 mm long, 3.0 mm across and 1.5 mm thick; color between RHS 165A and RHS 165B;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed.

It is claimed:

1. A new and distinct false indigo plant named *Baptisia* 'Pink Lemonade' as herein described and illustrated.

* * * * *